US006644967B2

United States Patent
Ceppatelli et al.

(10) Patent No.: US 6,644,967 B2
(45) Date of Patent: Nov. 11, 2003

(54) PROCESS FOR MAKING AN EXPANSION SCREW FOR ORTHODONTICS AND SCREW THUS MADE

(75) Inventors: Paolo Ceppatelli, Florence (IT); Maurizio Dolfi, Florence (IT); Gabriele Scommegna, Tavarnuzze (IT)

(73) Assignee: Leone S.p.A. (IT)

( * ) Notice: Subject to any disclaimer, the term of this patent is extended or adjusted under 35 U.S.C. 154(b) by 0 days.

(21) Appl. No.: 09/963,196

(22) Filed: Sep. 26, 2001

(65) Prior Publication Data
US 2002/0142259 A1 Oct. 3, 2002

(30) Foreign Application Priority Data
Apr. 2, 2001 (IT) .......................... FI01A0057

(51) Int. Cl.⁷ ................................................. A61C 7/10
(52) U.S. Cl. ....................................................... 433/7
(58) Field of Search ............................. 433/7, 18, 23, 433/24

(56) References Cited

U.S. PATENT DOCUMENTS

| 4,347,054 A | 8/1982 | Kraus et al. ............... 433/7 |
| 4,379,693 A | 4/1983 | Wallshein ................... 433/7 |
| 4,482,318 A | 11/1984 | Förster ....................... 433/7 |
| 4,571,177 A | * 2/1986 | Dahan ......................... 433/7 |
| 5,472,344 A | * 12/1995 | Binder et al. .............. 433/7 |
| 5,975,894 A | * 11/1999 | Pozzi ........................... 433/7 |

FOREIGN PATENT DOCUMENTS

FR     1 382 455     11/1964

* cited by examiner

*Primary Examiner*—Kevin Shaver
*Assistant Examiner*—Melba Bumgarner
(74) *Attorney, Agent, or Firm*—McGlew and Tuttle, P.C.

(57) ABSTRACT

The present invention refers to a process for making an expansion screw and a screw thus made; the expansion screw (100, 100') has two bodies (1, 2) that can be spaced apart by acting on the driving portion (6) of a double screw (3) housed within threaded central bores (30) provided in the two bodies (1, 2); each of the bodies (1, 2) has at least one bore (5, 50) parallel to the threaded bore; also provided is at least a hollow cylindrical guide (9) housed within a corresponding pair of parallel bores (5, 50) disposed on the two bodies (1, 2) in facing relationship; inserted in each guide (9) is a pin (4) for sliding therein; each guide (9) is fixed to one of the bodies, while the relevant pin (4) held therein is fixed to the other body, and the sliding of the pin (4) relative to the guide (9) takes place with friction owing to the force exerted upon assembly.

16 Claims, 13 Drawing Sheets

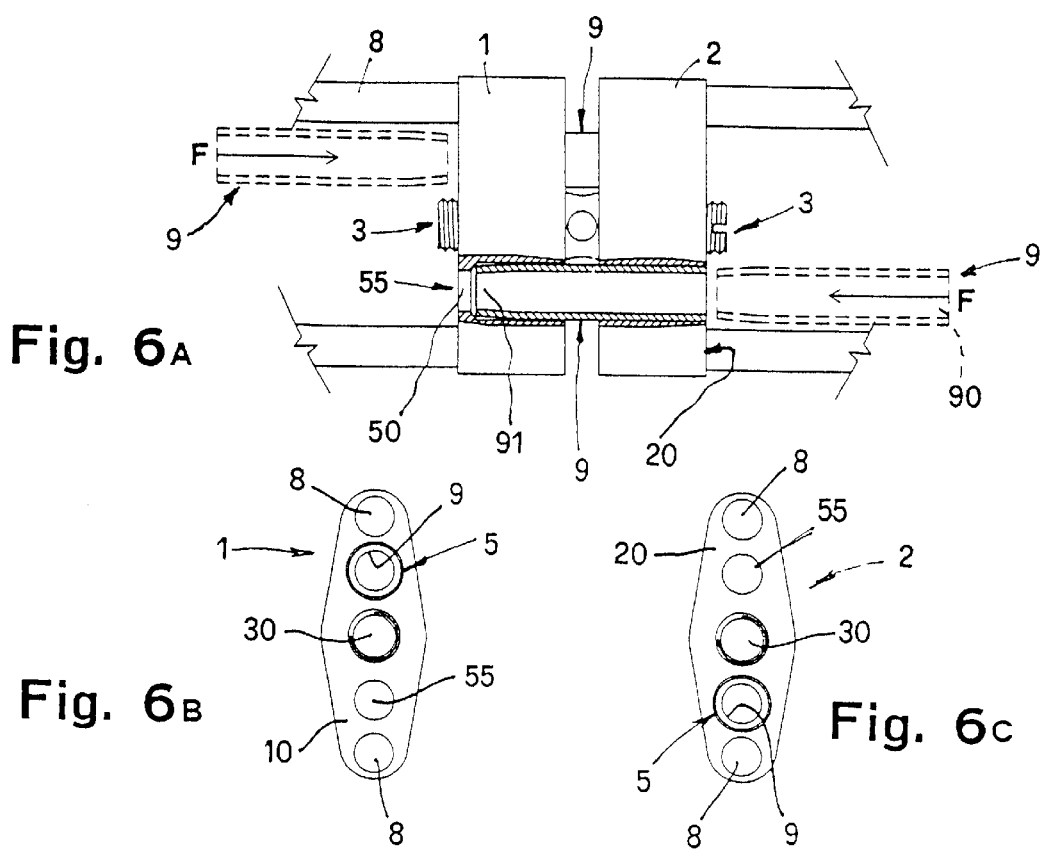

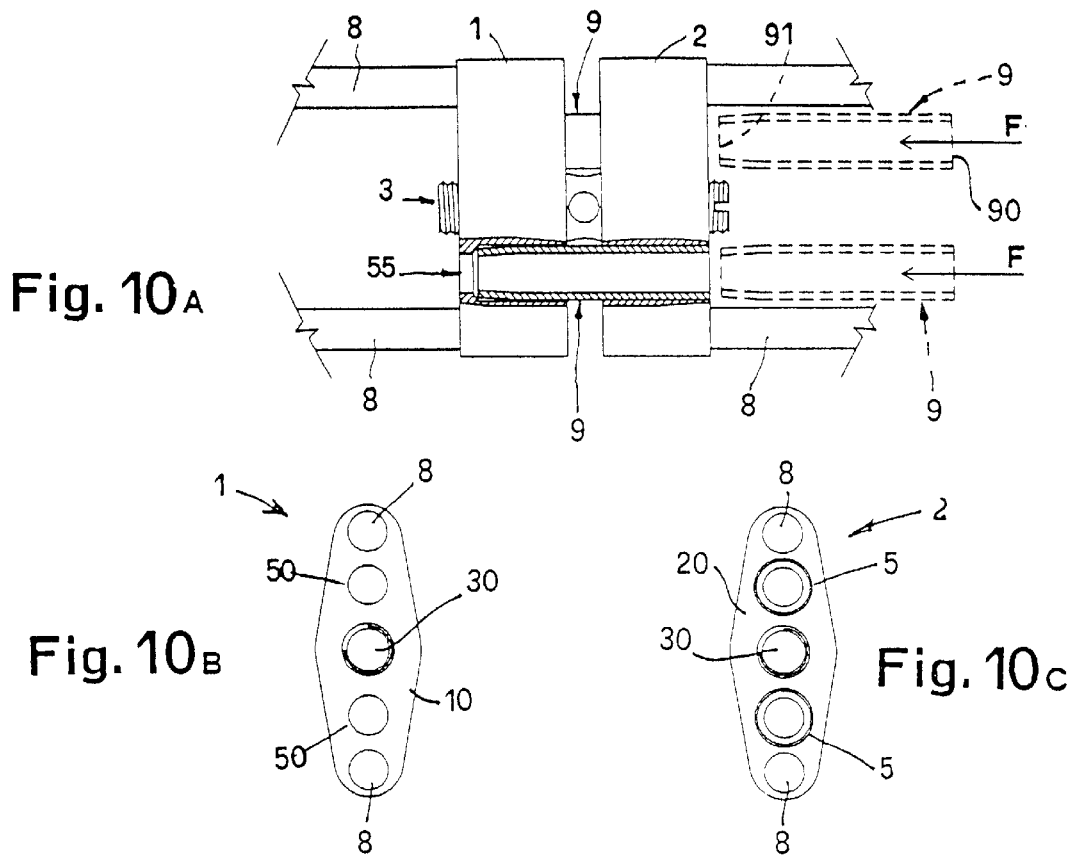

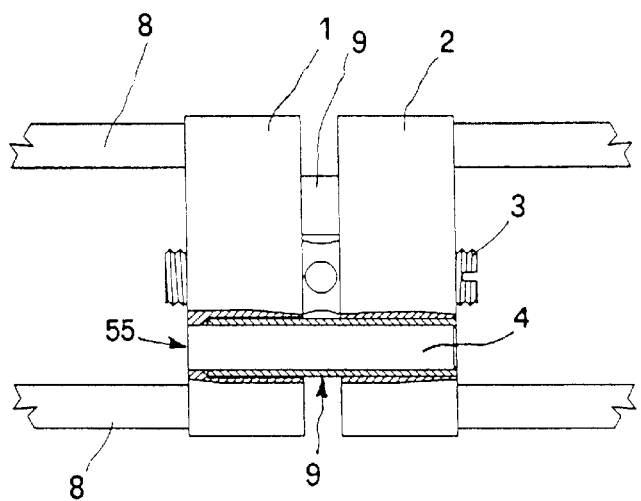
Fig.13A
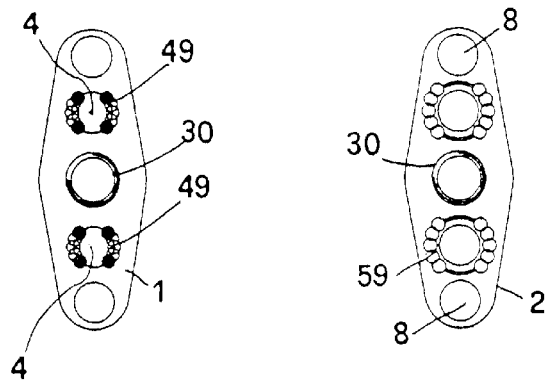
Fig. 13B
Fig.13C

PROCESS FOR MAKING AN EXPANSION SCREW FOR ORTHODONTICS AND SCREW THUS MADE

FIELD OF THE INVENTION

The present invention refers to a process for making an expansion screw for orthodontics and the orthodontic screw thus made.

BACKGROUND OF THE INVENTION

Shown in FIGS. 1 and 2 of the attached drawings is an example of expansion screw of known type for orthodontic use. The screw comprises, substantially, a bearing structure with two main bodies (1, 2) provided with arms (8) which allow it to be associated to orthodontic bands (or other component of different conformation and/or function) to complete an orthodontic apparatus to be used for expanding the palate by suitably displacing the two bodies (1, 2) apart. The said bodies (1, 2) exhibit a central bore (30) with inner left-hand threading by one side and a right-hand threading by the opposite side. The two bodies are disposed in facing relationship and connected to each other by a double screw (3) having a central portion (6), with a plurality of driving bores (7), which is intended to result in an intermediate position between the same bodies (1, 2). The adjustment of the operating condition of the apparatus, during the orthodontic treatment, is made by means of a suitable tool inserted within the bores (7) of said central portion. The said screw (3) is double, that is, it exhibits two threaded spindles, extending from opposite sides with respect to the central portion (6), each spindle is intended for engagement with the central threaded bore of one of said bodies (1, 2), so as to causes them to move away from, or close to each other depending on the [direction of] rotation into which the central portion (6) is driven during said adjustment. Moreover, the said main bodies (1, 2) exhibit, in addition to the threaded central bore, two more bores (5) parallel to the central one and extending from opposite sides with respect to the axis thereof. The additional bores (5), without threading, have two cylindrical guide pins (4) going therethrough.

When using the expansion screws of a so-called "free" type, because they are not immersed in the resin of a palate plate, a clearance is provided between the pins (4) and the bores (5), as necessary for the sliding of same pins and as a consequence of the work tolerances. In order to limit the negative effects of such clearance, the coupling between the central screw (3) and the threaded bores (30) which accomodate it is made by friction. In practice, chemicals of so-called "thread-braking" type are used to create a friction between the threaded spindles of the central screw and the threads mating therein. In this way, unwanted rotating movements of the central screw, likely to endanger the success of the orthodontic treatment, are counteracted.

A drawback related to this production technique stems from the fact that a thus treated screw cannot be subjected afterwards to any thermal or chemical treatments (such as those for cleaning or welding the bands) which would imply the suppression of the involved products with consequent suppression of the braking function they perform. Besides, the thread-braking chemicals may result in etching by substances present in the oral cavity and be dissolved.

A further drawback of the expansion screws of known type derives from the maximum extent of the expansion which cannot pass the physical limits of the length of the guide pins. Moreover, when positioning the apparatus in its maximum expansion configuration, the same apparatus may be somewhat unstable, since the pins (4) are almost entirely withdrawn from the relevant bores (5) (see FIG. 2).

A further drawback of the expansion screws of known type derives from the maximum extent of the expansion which cannot pass the physical limits of the length of the guide pins. Moreover, when positioning the apparatus in its maximum expansion configuration, the same apparatus may result somewhat unstable, since the pins (4) are almost entirely withdrawn from the relevant bores (5) (see FIG. 2).

A further (known) technique provides for deforming the threading of the nut screw which accomodates the threaded spindles of the central screw. However, in practice, it is impossible to ensure the same deformation all the time, so that, in some cases, a seizure effect may occur in the system after a brief period of use or, in other cases, the friction may result insufficient in relation to the work tolerances of the mating elements.

SUMMARY OF THE INVENTION

The main object of the present invention is to overcome the said drawbacks.

This result has been achieved, according to the invention, by providing an operating process and an orthodontic expansion screw having the characteristics indicated in the independent claims. Further characteristics being set forth in the dependent claims.

The advantages deriving from the present invention lie essentially in the fact that it is possible to ensure optimal stability and rigidity of the expansion screw when this is in use; that there is obtained a relatively wide expansion in relation to the overall dimensions of the screw; that the screw is safely retained in spite of its limited dimensions and expansion extent obtained (that is, with equal expansion, there is obtained a minor bulkiness of the guides and a larger mating surface, with respect to the known solutions); that the present screw can be subjected to physical and chemical treatments of sterilization or others, while maintaining its characteristics even after a prolonged service life.

BRIEF DESCRIPTION OF THE DRAWINGS

These and other advantages and characteristics of the present invention will be best understood by anyone skilled in the art from a reading of the following description in conjunction with the attached drawings given as a practical exemplification of the invention, but not to be considered in a limitative sense, wherein:

FIGS. 6A, 6B, 6C show, respectively, a plan view with parts taken away, a right side view and a left side view relating to a step of a possible embodiment of the process according to the invention;

FIGS. 10A, 10B, 10C show, respectively, a plan view with parts taken away, a right side view and a left side view relating to a step of a further possible embodiment of the process according to the invention;

FIGS. 13A, 13B, 13C show, respectively, a plan view with parts taken away, a right side view and a left side view relating to a step subsequent to that of FIGS. 12A–12C;

DESCRIPTION OF THE PREFERRED EMBODIMENTS

Figure 1:
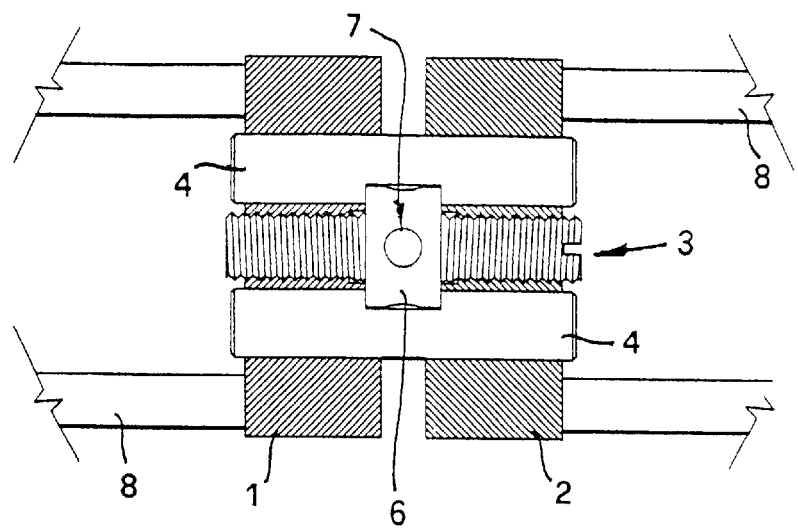
FIGS. 1 and 2 are schematic sectional views with parts taken away of one embodiment of the orthodontic expansion screw of known type, respectively in a minimum and maximum bulkiness configuration.
Figure 2:
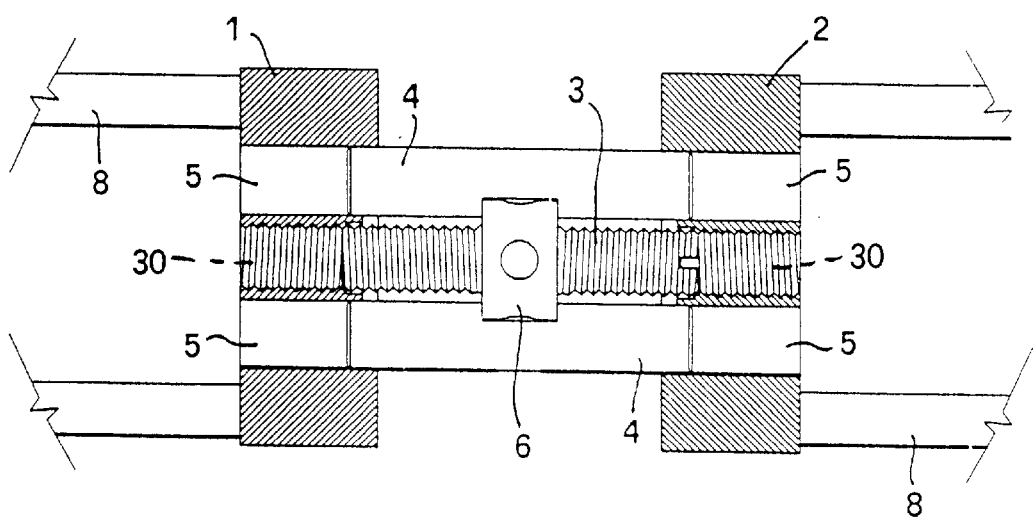
Figure 3:
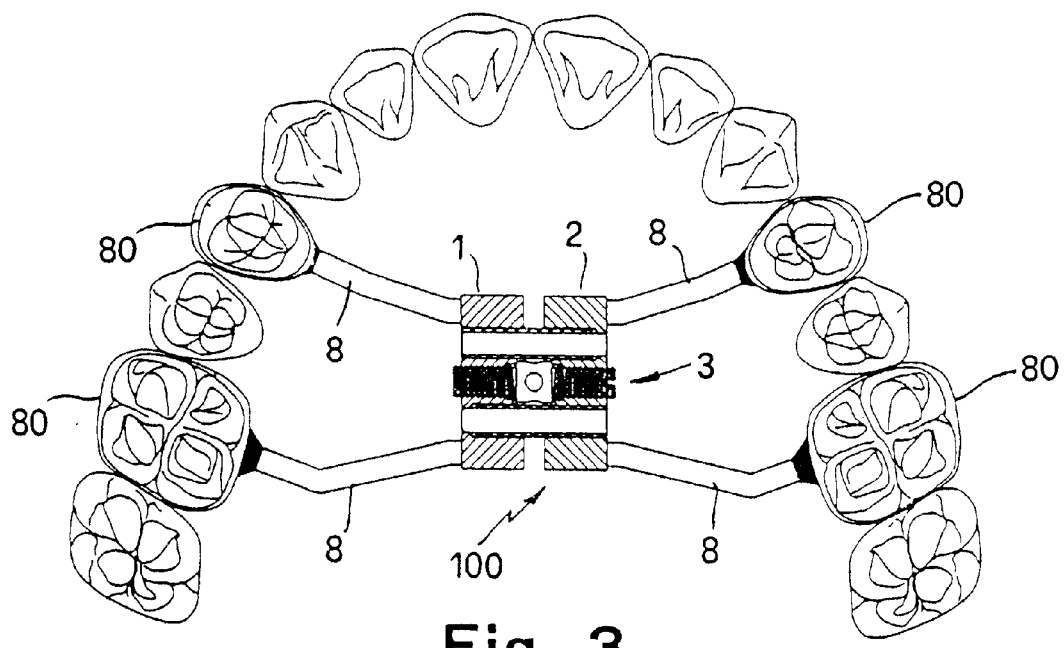
FIG. 3 is a plan view, with parts taken away and in section, of one example of application of the present invention to a dental arch.
Figure 4:
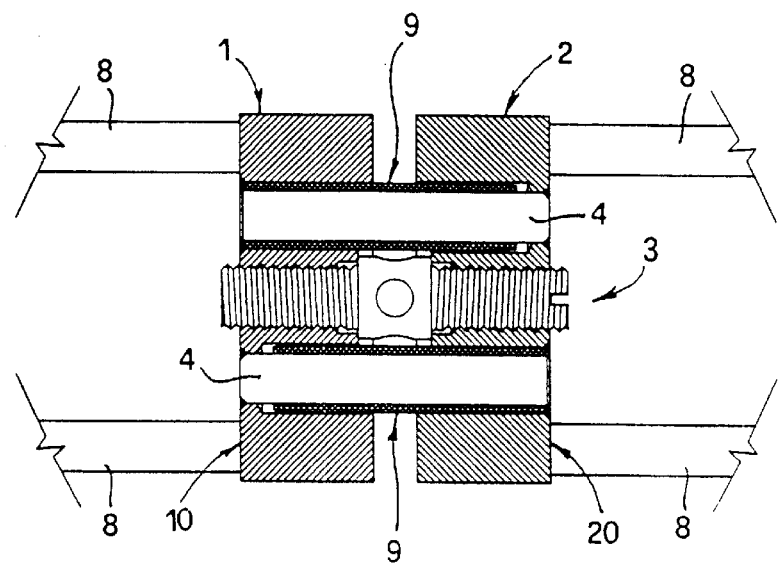
FIGS. 4 and 5 are schematic plan views in horizontal section, with parts taken away, of one embodiment of the orthodontic expansion screw according to the present invention, respectively in a minimum and maximum bulkiness configuration.

With reference to the figures of the attached drawings, which figures, for sake of clarity, are not all in the same scale, the process in question can be implemented for making an orthodontic expansion screw of a type comprising two main bodies (1, 2) having a threaded central bore (30) and two side bores (5, 50). The threaded bores (30) are able to receive a double screw (3), while the side bores (5) are provided for housing two cylindrical guide pins (4).

The attached drawings show two possible embodiments of the present method, respectively in FIGS. 3–9C and 10A–13C. In the description that follows, although reference is made directly to FIGS. 3–13C, it is understood that a similar process makes it possible to provide also the other embodiment of screw (100') represented in FIGS. 14–17 and having only two bores (5, 50).

With reference to the figures showing the nonlimitative examples of the accompanying drawings, the process includes the operating steps described herebelow.

The two main bodies (1, 2) are made by forming on each of them the threaded central bore (30) and two side bores parallel to the central one, so that the whole of the two bodies exhibits two threaded central bores (30), intended to accomodate the central screw (3), and four side bores (5, 50). In the examples, each of the two bodies (1, 2) has two arms (8) to be associated either with orthodontic bands (80) or with other suitable means for fixing and/or connecting the teeth of a dental arch. In the case of the screw (100') depicted in FIGS. 14–17, only one, non threaded bore will be formed on the bodies (1, 2); in particular, a one-diameter bore (5) on the body (1) and a diameter-varying bore (50) on the body (2). Moreover, only one arm (8) is provided for each of bodies (1, 2).

In particular, the central bore (30) is formed in the same way as provided by the known technique, inasmuch as it is the double screw (3) to be associated therewith. In the example of FIGS. 3–9C, two differently shaped side bores (5, 50) are formed for each of the bodies (1, 2): one of said bores (5), for example the one located in the upper part of the body (1), like the one located in the lower part of body (2), has a constant diameter (D5); the other bore (50) of each body has a constant diameter (D5), the same as diameter (D5) of the first bore (5), in correspondence of a first section (54) and for an extension of predetermined length, while exhibiting a minor diameter (D55) in correspondence of the opposite section (55), that is, of the section which results on the outer wall (10, 20) of body (1, 2). In the example of FIGS. 10A–13C, instead, the body (1) has both bores (50) with varying diameter, while the body (2) has the two bodies of constant diameter (5). In the example of FIGS. 14–17, in which the screw (100') is represented in assembled condition, the body (1) has a bore (5) of constant diameter, while the body (2) has a bore (50) of varying diameter.

The two bodies (1, 2) are disposed in facing relationship, so as to allign a constant-diameter side bore (5) of one body with a diameter-varying bore (50) of the other body, by screwing the double screw (3) as necessary within the corresponding threaded bores (30) formed in the two bodies (1, 2) and thus connecting the latter to each other.

Then two cylindrical hollow guides (9) are used which have, along their longitudinal development, a constant inner diameter substantially corresponding to the said minor diameter (D55), while, in correspondence of a first or leading end (91) they exhibit, at lest internally, a reduced diameter. Each cylindrical hollow guide (9) is inserted, on the side of its leading end (91), into the constant-diameter bore (5) of one body (1, 2) and, then, into the bore (50) of the other body. Obviously, the outer diameter of the guides (9) is such as to allow the insertion thereof within the bores (5, 50). In practice, each guide (9) goes through the body having constant-diameter bore (5) to enter the opposite bore (50) formed in the other body. This step is illustrated in FIGS. 6A–6C for the first example, and in FIGS. 10A–10C for the second wherein the arrow (F) indicates the directions of insertion of the guides (9).

Thereafter, each cylindrical guide (9) is fixed to one of said bodies (1, 2) in correspondence of the opposite or trailing side (90). The fixing can be carried out by laser, as best visible in FIGS. 7B, 7C and 11C, wherein the laser-welded spots are indicated with numeral (59). The fixing of the hollow guides (9) to the bodies (1, 2) is made in correspondence of the trailing end (90) thereof, this end being disposed substantially flush with the outer wall (10, 20) of the body to which it is fixed.

Figure 8A:
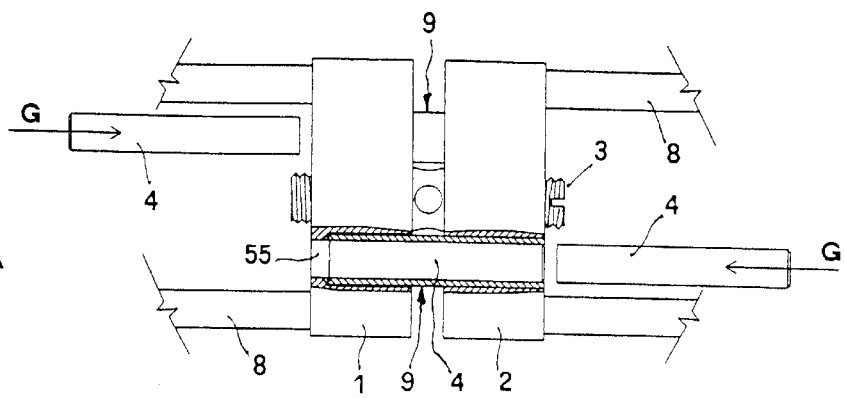
FIGS. 8A, 8B, 8C show, respectively, a plan view with parts taken away, a right side view and a left side view relating to a step subsequent to that of FIGS. 7A–7C.
Figure 8B:
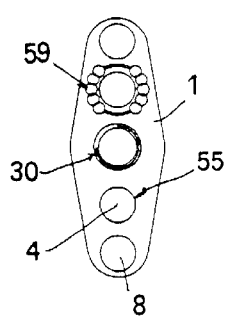
Figure 8C:
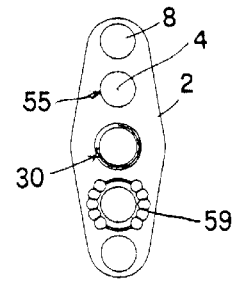
Figure 8D:
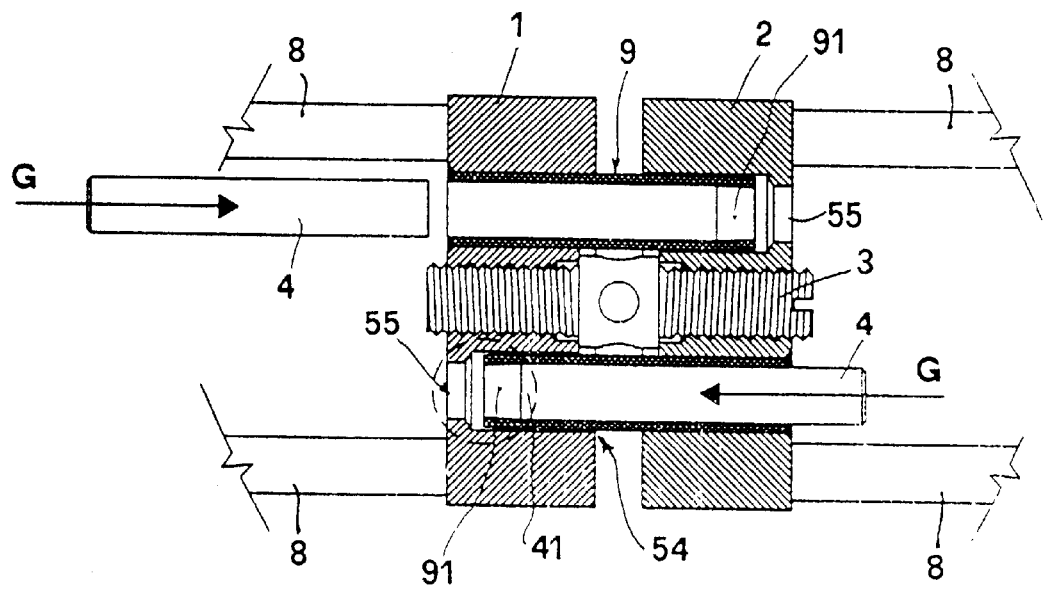
FIG. 8D shows a plan view in horizontal section of the embodiment of FIG. 8A.
Figure 8E:
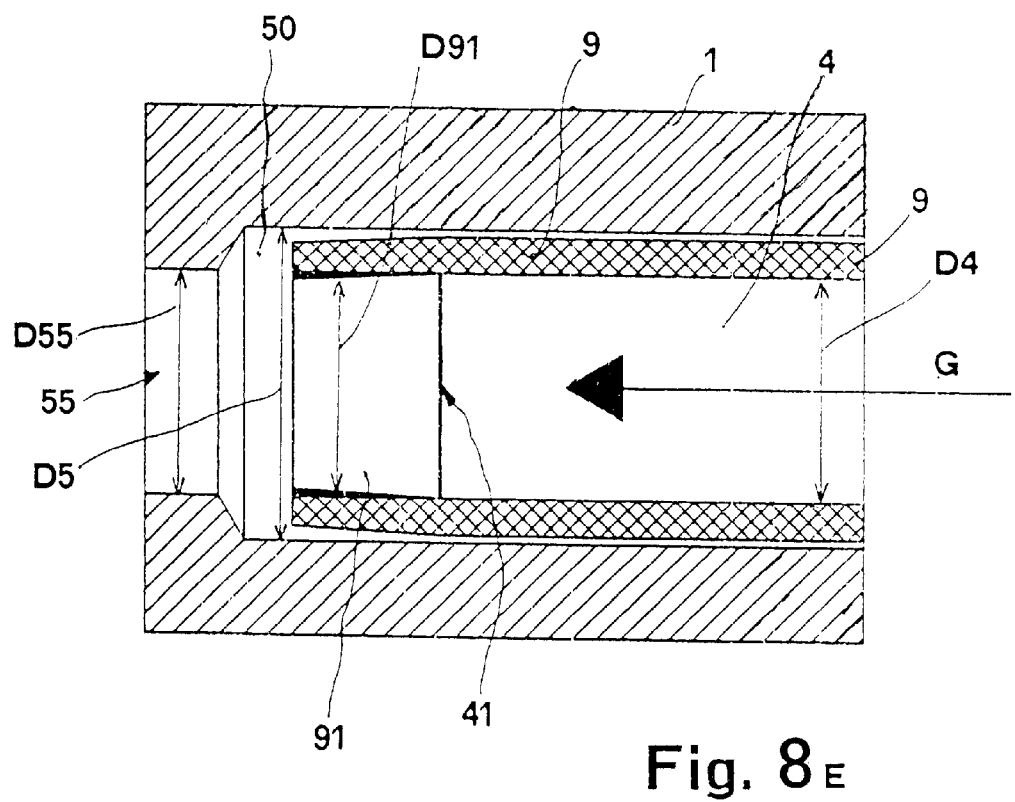
FIG. 8E is an enlarged detail of the area encircled by a broken line in FIG. 8D.
Figure 12A:
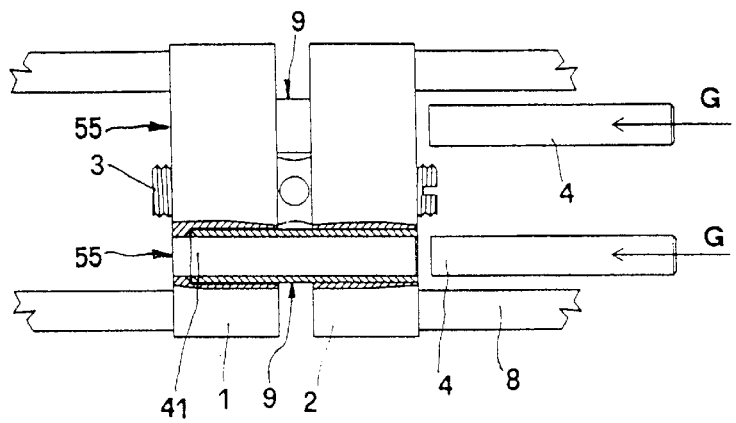
FIGS. 12A, 12B, 12C show, respectively, a plan view with parts taken away, a right side view and a left side view relating to a step subsequent to that of FIGS. 11A–11C.
Figure 12B:
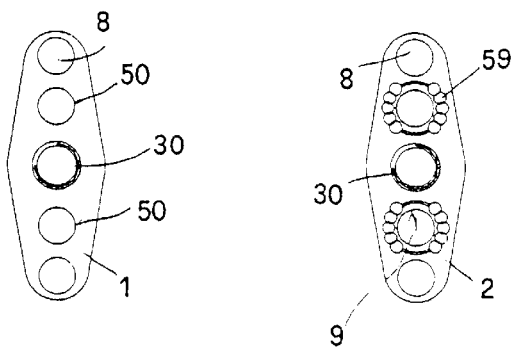
Figure 12C:
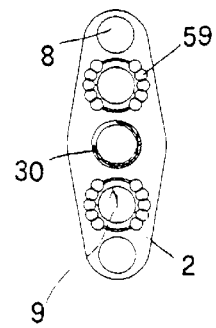

Afterwards, a cylindrical pin (4) is inserted into each cylindrical hollow guide (9) through the relevant trailing end (90), as indicated by the arrows (G) in FIGS. 8A and 12A. The outer diameter (D4) of each pin (4) corresponds substantially to said minor diameter (D55) of diameter-varying bores (50) formed in said bodies (1, 2); each pin (4) is inserted into the relevant guide (9) as far as its leading end (41) reaches the end (91) of same guide. The said pins (4) are pushed further through said end (91) of the hollow guides (9), with some force to win the interference due to the difference of the respective diameters (D4, D91), and as far as to have the leading end (41) of pins (4) in correspondence of the outer section (55) of the relevant bore (50). This step being shown in FIGS. 8A and 12A.

Figure 9A:
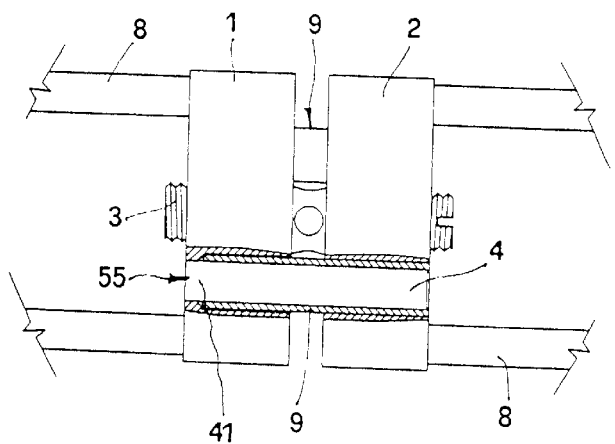
FIGS. 9A, 9B, 9C show, respectively, a plan view with parts taken away, a right side view and a left side view relating to a step subsequent to that of FIGS. 8A–8C.
Figure 9B:
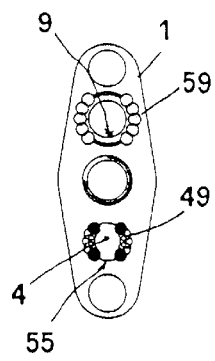
Figure 9C:
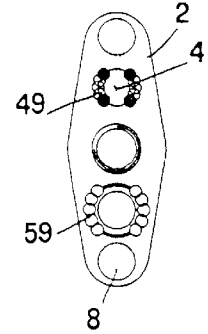
Figure 11A:
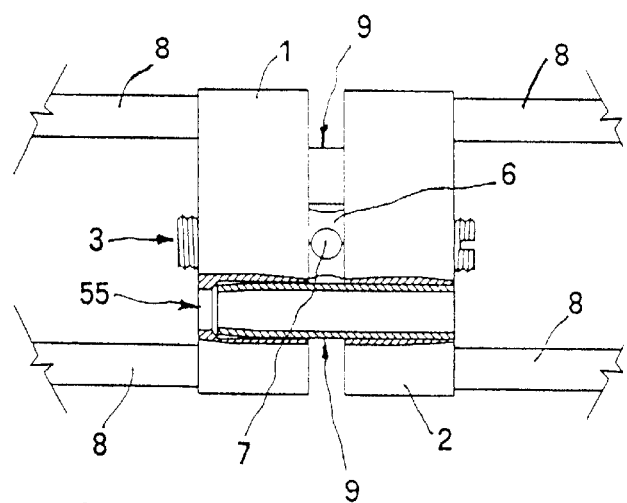
FIGS. 11A, 11B, 11C show, respectively, a plan view with parts taken away, a right side view and a left side view relating to a step subsequent to that of FIGS. 10A–10C.
Figure 11B:
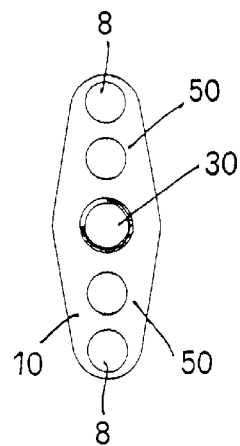
Figure 11C:
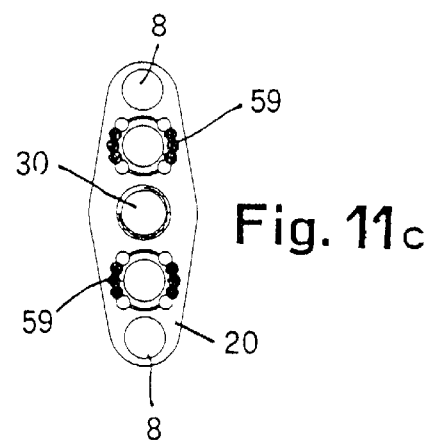

The leading ends of the two pins (4) are then fixed to the respective bodies (1, 2) in correspondence of said leading section (55) by laser-welding, for example, as best shown in FIGS. 9B, 9C and 13B wherein numeral (49) indicates the laser-welding spots.

In this way there is obtained an expansion screw (100) which has two bodies (1, 2) that can be spaced apart by means of a known per se driving tool fitted into the bores (7) of the driving portion (6) of double screw (3) to drive the latter into rotation, according to an expansion program as established by the doctor; each of said bodies (1, 2) of the expansion screw (100) has two side bores which may be either different to each other, as in the example relevant to the first embodiment of the method (see FIGS. 3–9C), or equal to each other, as in the second example (see FIGS. 10A–13C). In each of said side bores (5, 50) a guide (9) is provided for a pin (4) to slide therein. Each guide (9) is fixed to one of said bodies, while the relevant pin (4) present therein is fixed to the other body; the sliding of the pin relative to the guide takes place with some friction owing to the force exerted upon assembly.

With reference to the example of FIGS. 14–17, the expansion screw (100') thus obtained exhibits two bodies (1, 2) displaceable from each other by means of a drive tool, known per se, fitted into the bores (7) of the driving portion (6) of double screw (3) to drive the latter into rotation, according to an expansion program as established by the doctor; each of said bodies (1, 2) of the expansion screw (100) has one bore: in particular, the body (1) has a constant-diameter bore (5) and the body (2) has a diameter-varying bore (2). Within the bores (5, 50) there is a guide (9) for a pin (4) to slide therein. The guide (9) is fixed to the body (1), while the relevant pin (4) held therein is fixed to the other body (2); numerals (59) and (49) in FIG. 15 indicate the possible sites for fixing. The sliding of the pin relative to the guide takes place with some friction owing to the force exerted upon assembly.

It will be appreciated that the stability and rigidity of the thus made screws (100, 100') are remarkable even in case the central screw (3) is not subjected to specific treatments. The friction between each guide (9) and relevant pin (4) is such as to prevent spontaneous and undesired rotations of the screw (3) when in operative condition. It should be noted, in particular, the fact that the association between guides and pins is made with tolerances hardly obtainable by other working processes, and this because each pin is in fact inserted into its relevant guide by force, as above mentioned.

Moreover, the expansion of screw (100) is quite broad, as the lengths of the guides and those of the pins sum up by giving rise to a sort of telescopic connection between the bodies (1, 2), which determines coupling surfaces much extended between the guides and the pins also under maximum expansion condition.

Figure 5:
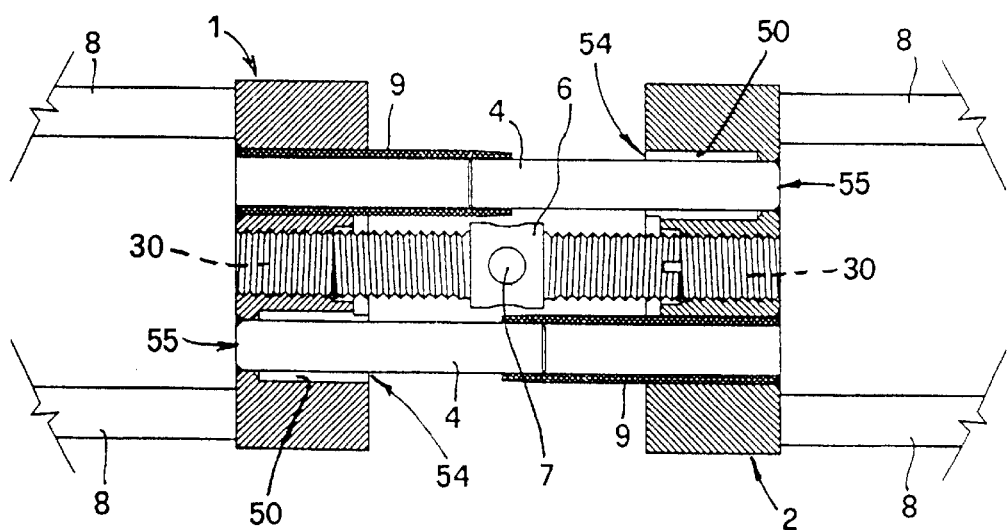
Figure 7A:
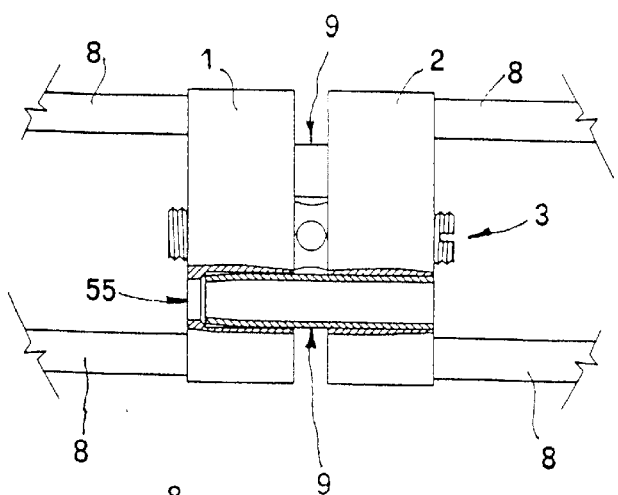
FIGS. 7A, 7B, 7C show, respectively, a plan view with parts taken away, a right side view and a left side view relating to a step subsequent to that of FIGS. 6A–6C.
Figure 7B:
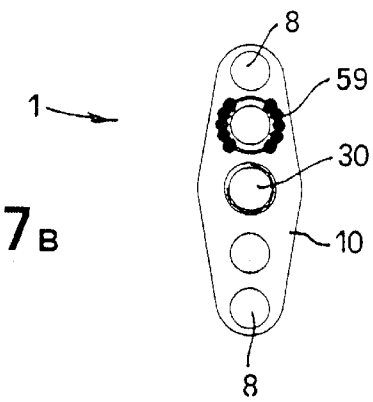
Figure 7C:
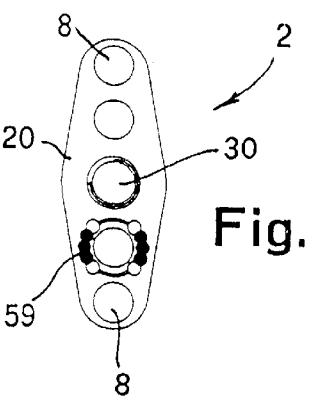
Figure 15:
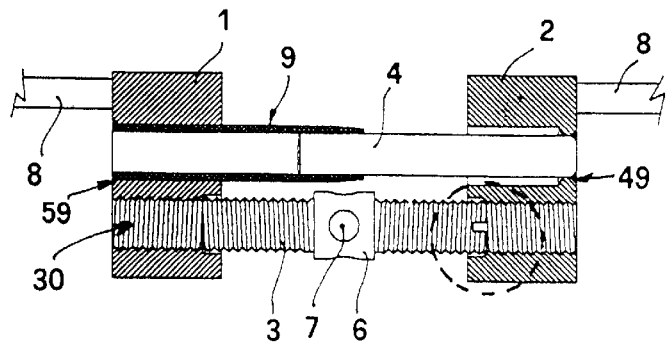
FIGS. 14 and 15 are schematic plan views in horizontal section, with parts taken away, of a further embodiment of the orthodontic expansion screw according to the present invention, respectively in a minimum and maximum bulkiness configuration.
Figure 14:
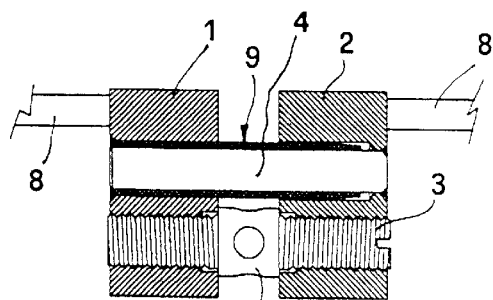
Figure 16:
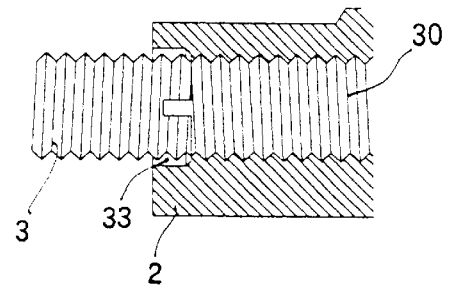
FIG. 16 is an enlarged detail of the area encircled by a broken line in FIG. 15.
Figure 17:
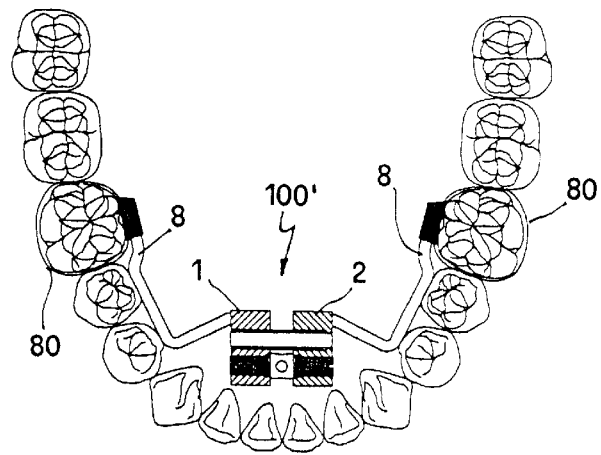
FIG. 17 is a plan view in section, with parts taken away, of one example of application of the screw of FIGS. 14–16.

Under a condition of maximum expansion, as shown in FIGS. 5 and 15, it is not possible either to contract or expand any longer the screw, since the spindles of the central screw (3) result outside the threadings (30). As best viewable in the detail of FIG. 16, when the screw (100, 100') is in its condition of maximum expansion, the two ends of screw (3) lie in an inner, non-threaded, terminal region (33) of the bore (30). However, even when taking such configuration, the screw results all the same stable and rigid thanks to the length of pins (4) which allows them to remain housed within the guides (9). Accordingly, the advantages offered by the present screw make it possible to ensure a correct and safe orthodontic treatment while preventing any accidental disassembly of the same screw within the patient's mouth.

The construction details may vary in any equivalent way as far as the shape, dimensions, elements disposition, nature of the used materials are concerned, without nevertheless departing from the scope of the adopted solution idea and, thereby, remaining within the limits of the protection granted to the present patent.

What is claimed is:

1. A process for making an orthodontic expansion screw, the process comprising the steps of:

forming two main bodies each with a threaded bore and a parallel bore parallel to the threaded bore;

providing a double screw with a driving portion, the double screw having first and second spindles respectively fitting into a respective one of said threaded bores;

providing a guidepin disposed coaxial to each said parallel bore, said guide pin having a leading end and a trailing end;

disposing the two bodies in facing relationship so as to align opposite parallel bores by screwing the double screw within the corresponding threaded bores to connect the two bodies to each other to provide facing walls of the two bodies and to provide opposite outer walls of the two bodies;

inserting into the aligned opposite bores a hollow cylindrical guide having a leading end and a trailing end, an outer diameter of the guide pin being slightly greater than a leading end inner diameter of the hollow cylindrical guide;

fixing the trailing end of the hollow cylindrical guide to one of said bodies at or adjacent to the outer wall of said one of said bodies;

inserting the guide pin into the hollow cylindrical guide through the cylindrical guide trailing end and positioning the leading end of the guide pin in correspondence to the leading end of said hollow cylindrical guide and pushing the leading end of the guide pin through the leading end inner diameter of said hollow cylindrical guide by the application of force to overcome the interference due to a difference of the respective diameters; and fixing the leading end of the guide pin to the other of said bodies at or adjacent to the outer wall of said other of said bodies.

2. A process according to claim 1, further comprising:

forming another parallel bore parallel to the threaded bore;

providing another guide pin disposed coaxial to each said another parallel bore, said another guide pin having a leading end and a tailing end;

during the step of disposing the two bodies in facing relationship aligning the opposite another parallel bores during the screwing of the double screw within the corresponding threaded bores for connecting the two bodies to each other;

inserting into the aligned another parallel bores another hollow cylindrical guide having a leading end and a trailing end, an outer diameter of the another guide pin being slightly greater than a leading end inner diameter of the another hollow cylindrical guide;

fixing the tailing end of the another cylindrical guide to one of said bodies at or adjacent to the outer wall of said one of said bodies;

inserting the another guide pin into the another hollow cylindrical guide though the cylindrical guide trailing end and positioning the leading end of the another guide pin in correspondence to the leading end of said another hollow cylindrical guide and pushing the leading end of said another guide pin through the leading end inner diameter of said another hollow cylinder by the application of force to overcome the interference due to a difference of the respective diameters; and fixing the leading end of the another guide pin to the other of said bodies at or adjacent to the outer wall of said other of said bodies.

3. A process according to claim 1, further comprising:

forming another parallel bore in each of the two main bodies each with the parallel bores of the two main bodies including two parallel bores having a constant diameter parallel to the threaded bore and including two parallel bores of varying diameter parallel to the threaded bore, each of the parallel bores of varying diameter having a first section of constant diameter and a second section of reduced diameter;

providing another guide pin having a leading end and a trailing end;

during the step of disposing the two bodies in facing relationship aligning each parallel bore of constant diameter with a parallel bore of varying diameter opposite, during the screwing of the double screw within the corresponding threaded bores for connecting the two bodies to each other;

providing another hollow cylindrical guide;

inserting each hollow cylindrical guide into the parallel bore of constant diameter of one body and thereafter into the parallel bore of varying diameter of the other body;

fixing each cylindrical guide to one of said bodies;

inserting one of the guide pins into each hollow cylindrical guide and pushing each pin with a force to overcome interference due to a difference of diameters of the threaded bores; and fixing the leading end of each guide pin to one of said bodies.

4. A process according to claim 3, wherein the two main bodies are formed each with the threaded bore and another threaded bore.

5. A process according to claim 4, wherein one parallel bore of varying diameter is formed in each main body.

6. A process according to claim 4, wherein both parallel bores of varying diameter are formed on the same main body.

7. A process according to claim 4, wherein each of said hollow cylindrical guides is fixed to one of the bodies by laser-welding.

8. A process according to claim 1, wherein each of the guide pins is fixed to one of the bodies by laser-welding.

9. An orthodontic expansion screw comprising:

two main bodies each having a threaded central bore and a parallel bore, parallel to said central bore;

a double screw with a driving portion and spindles, each of the spindles engaging a respective one of said threaded bores of said two main bodies;

a guide pin disposed coaxial to each said parallel bore of said two main bodies;

a hollow cylindrical guide disposed within said parallel bore of one of said two main bodies and fixed to said one of said two main bodies and freely extendable through said parallel bore of the other of said two main bodies, said guide pin being inserted with an interference fit into said hollow cylindrical guide wherein an outer diameter of said guide pin is larger than an inner diameter of at least a portion of said hollow cylindrical guide prior to insertion to provide frictional contact between an outer surface of said guidepin and an inner surface of said portion of said hollow cylindrical guide, said guide pin being fixed to said other of said two main bodies.

10. An orthodontic expansion screw according to claim 9, further comprising:

another parallel bore in each of said two main bodies, said parallel bore and said another parallel bore in each of said two main bodies forming first and second side bores parallel to said threaded central bore of said two main bodies;

another guide pin disposed coaxial to said second side bore of each of said two main bodies;

another hollow cylindrical guide fixed to one of said two bodies and disposed in said second side bore of said one of said two bodies and freely going through the other second side bore of the other of said two bodies, said another guide pin being inserted with an interference fit into said another hollow cylindrical guide wherein an outer diameter of said another guide pin is larger than an inner diameter of at least a portion of said another hollow cylindrical guide prior to insertion to provide frictional contact between an outer surface of said another guide pin and an inner surface of said portion of said another hollow cylindrical guide, said another guide pin being fixed to said other second parallel bore of said two main bodies.

11. An orthodontic expansion screw comprising:

a first body having a threaded central bore and a parallel side bore, parallel to said central bore;

a second body having a threaded central bore and a parallel side bore, parallel to said central bore;

a double screw with a driving portion and a first spindle engaging said first body threaded bore and a second spindle engaging said second body threaded bore wit said first body and said second body having facing sides;

a guide pin disposed coaxial to each of said first body parallel side bore and said second body parallel side bore;

a hollow cylindrical guide disposed within said first body parallel side bore and fixed to said first body and freely extendable through said second body, said guide pin being inserted with an interference fit into said hollow cylindrical guide wherein an outer diameter of said guide pin is larger than an inner diameter of at least a portion of said hollow cylindrical guide prior to insertion to provide frictional contact between an outer surface of said guide pin and an inner surface of said portion of said hollow cylindrical guide, said guide pin being fixed to said second body, at least one of said first body parallel side bore and said second body parallel side bore having a constant diameter and the other of said first body parallel side bore and said second body parallel side bore having a varying diameter with a constant diameter first section extending a predetermined length and a second section, opposite to said first section, with a smaller minor diameter, said second section being opposite said facing sides.

12. An expansion screw according to claim 11, further comprising:

another parallel side bore in each of said first body and said second body;

another guide pin disposed coaxial to said another side bore of each of said first body and said second body;

another hollow cylindrical guide fixed to one of said first body and said second body and disposed in said another side bore of one of said first body and said second body and freely extending through the another side bore of the other of said first body and said second body, said another guide pin being inserted with an interference fit into said another hollow cylindrical guide wherein an outer diameter of said another guide pin is larger than an inner diameter of at least a portion of said another hollow cylindrical guide prior to insertion, to provide frictional contact between an outer surface of said another guide pin and an inner surface of said portion of said another hollow cylindrical guide, said another guide pin being fixed to said other of said first body and said second body, at least one of said first body another parallel side bore and said second body another parallel side bore having a constant diameter and the other of said first body another parallel side bore and said second body another parallel side bore having a varying diameter with a constant diameter first section extending a predetermined length and an opposite section with a smaller minor diameter, said opposite section being opposite said facing sides.

13. An expansion screw according to claim 12, wherein said first body has said parallel side bore having a constant diameter and said second body has said another parallel side bore having a constant diameter.

14. An expansion screw according to claim 12, wherein said first body has each of said parallel side bore having a varying diameter and said another parallel side bore having a varying diameter.

15. An expansion screw according to claim 11, wherein said hollow cylindrical guide has a constant outer diameter, substantially corresponding to said minor diameter of said bore of varying diameter along a longitudinal development thereof and a reduced internal diameter in a section of a leading end.

16. An expansion screw according to claim 11, wherein said guide pin has an outer diameter substantially corresponding to a minor diameter of said bore of varying diameter.

* * * * *